US 7,229,611 B2

(12) United States Patent
Zamudio-Tena et al.

(10) Patent No.: US 7,229,611 B2
(45) Date of Patent: Jun. 12, 2007

(54) CLEAR PERSONAL CARE COMPOSITIONS CONTAINING VISIBLE CAPSULES

(75) Inventors: Jose F. Zamudio-Tena, Westwood, MA (US); Gordon G. Guay, Chelmsford, MA (US); Tuan M. Vu, Canton, MA (US); John Anderson, North Andover, MA (US)

(73) Assignee: The Gillette Company, Boston, MA (US)

( * ) Notice: Subject to any disclaimer, the term of this patent is extended or adjusted under 35 U.S.C. 154(b) by 497 days.

(21) Appl. No.: 10/632,407

(22) Filed: Aug. 1, 2003

(65) Prior Publication Data

US 2004/0047822 A1 Mar. 11, 2004

(51) Int. Cl.
*A61Q 15/00* (2006.01)
*A61K 8/02* (2006.01)
*A61K 9/127* (2006.01)

(52) U.S. Cl. .................. 424/65; 424/400; 424/401; 424/450

(58) Field of Classification Search ................ 424/65, 424/400, 401, 450
See application file for complete search history.

(56) References Cited

U.S. PATENT DOCUMENTS

| | | | |
|---|---|---|---|
| D27,864 S | 11/1897 | Blackman | |
| 692,481 A | 2/1902 | Robinson | |
| 964,422 A | 7/1910 | Hood | |
| 1,669,016 A | 5/1928 | O'Neil | |
| 1,791,359 A | 2/1931 | Henriksen | |
| 2,101,540 A | 12/1937 | Gullich | |
| 2,165,420 A | 7/1939 | Siefert | |
| 2,174,779 A | 10/1939 | Delorme | |
| 2,613,185 A | 10/1952 | Marshall | |
| 2,970,083 A | 1/1961 | Bell | |
| D201,229 S | 5/1965 | Burke | |
| 3,294,692 A | 12/1966 | Kelly et al. | |
| 3,479,429 A | 11/1969 | Morshauser et al. | |
| 4,120,948 A | 10/1978 | Shelton | |
| 4,126,674 A | 11/1978 | Mausner | |
| 4,202,879 A | 5/1980 | Shelton | |
| 4,393,643 A | 7/1983 | Fryar et al. | |
| 4,511,552 A | 4/1985 | Cox | |
| 4,524,062 A | 6/1985 | Laba et al. | |
| 4,578,207 A | 3/1986 | Holdt et al. | |
| 4,714,085 A | 12/1987 | von Kleinsorgen | |
| 4,743,443 A | 5/1988 | Pisani et al. | |
| 4,786,449 A | 11/1988 | Smit | |
| 4,803,195 A * | 2/1989 | Holzner .................. 512/4 |
| 4,879,063 A | 11/1989 | Wood-Rethwill et al. | |
| 5,000,947 A * | 3/1991 | Nichols ................ 424/69 |
| 5,217,639 A | 6/1993 | Mottola | |
| D344,154 S | 2/1994 | Mottola | |
| 5,290,570 A * | 3/1994 | Nichols ................ 424/499 |
| 5,330,751 A | 7/1994 | Curtin et al. | |
| 5,417,964 A | 5/1995 | Carlson, Sr. et al. | |
| 5,538,161 A | 7/1996 | Koehler et al. | |
| 5,587,153 A * | 12/1996 | Angelone et al. ............. 424/66 |
| 5,705,171 A | 1/1998 | Iovanni et al. | |
| 5,759,974 A | 6/1998 | Menke et al. | |
| 5,965,501 A | 10/1999 | Rattinger | |
| D423,713 S | 4/2000 | Szekely | |
| D430,346 S | 8/2000 | van der Hagen | |
| 6,096,296 A | 8/2000 | Alflen et al. | |
| D443,951 S | 6/2001 | Look | |
| D444,264 S | 6/2001 | Look | |
| D444,265 S | 6/2001 | Look | |
| 6,245,325 B1 | 6/2001 | Shen | |
| D444,593 S | 7/2001 | Look | |
| D444,913 S | 7/2001 | Look | |
| D446,356 S | 8/2001 | Look | |
| D446,606 S | 8/2001 | Look | |
| D446,607 S | 8/2001 | Look | |
| D454,227 S | 3/2002 | Look | |
| D454,228 S | 3/2002 | Look | |
| D454,229 S | 3/2002 | Look | |
| D454,414 S | 3/2002 | Look | |
| D454,661 S | 3/2002 | Look | |
| D454,662 S | 3/2002 | Look | |
| D454,663 S | 3/2002 | Look | |
| D454,664 S | 3/2002 | Look | |
| D454,665 S | 3/2002 | Look | |
| D454,666 S | 3/2002 | Look | |
| D454,983 S | 3/2002 | Look | |
| D454,984 S | 3/2002 | Look | |
| D454,985 S | 3/2002 | Look | |
| 6,534,091 B1 | 3/2003 | Garces Garces et al. | |
| D475,616 S | 6/2003 | Lambrecht | |

(Continued)

FOREIGN PATENT DOCUMENTS

CA 2309334 10/1998

(Continued)

OTHER PUBLICATIONS

The Body Shop Skin & Hair Care Products catalog holiday edition c 1995; p. 16 makeup indicated by arrows.

*Primary Examiner*—Shelly A. Dodson
(74) *Attorney, Agent, or Firm*—Andrew J. Hagerty; Tara M. Rosnell; Brian M. Bolam

(57) ABSTRACT

Disclosed are clear antiperspirant or deodorant compositions that include visible capsules.

23 Claims, 1 Drawing Sheet

U.S. PATENT DOCUMENTS

2002/0159957 A1  10/2002  Lages et al.

FOREIGN PATENT DOCUMENTS

| | | |
|---|---|---|
| DE | 199 21 183 A1 | 9/2000 |
| EP | 1 184 027 | 3/2002 |
| FR | 977194 | 3/1951 |
| FR | 2786408 | 6/2000 |
| GB | 2014507 A | 2/1979 |
| GB | D2081820 | 7/1999 |
| JP | 3 014514 | 1/1991 |
| WO | WO 92/00722 | 1/1992 |
| WO | WO 99/23998 | 5/1999 |
| WO | WO 00/19861 | 4/2000 |
| WO | WO 00/40212 | 7/2000 |
| WO | WO 01/05358 | 1/2001 |
| WO | WO 02/26204 A2 | 4/2002 |
| WO | WO 03/020865 | 3/2003 |

* cited by examiner

CLEAR PERSONAL CARE COMPOSITIONS CONTAINING VISIBLE CAPSULES

TECHNICAL FIELD

This invention relates to clear personal care compositions containing visible capsules.

BACKGROUND

Antiperspirant and deodorant compositions are well known personal care products. The compositions come in a variety of forms and may be formulated, for example, into aerosols, pumps, sprays, liquids, roll-on, lotions, creams, gels, and sticks (both hard and soft).

It is known that clear antiperspirant and deodorant compositions are desirable for aesthetic reasons. Three techniques generally have been used to provide such clear compositions. One technique involves matching the refractive indices of two immiscible phases in an emulsion. A second technique involves solidifying a solution with an clear gellant. A third technique involves forming a microemulsion of immiscible components.

Various cosmetic products containing microcapsules are known. For example, U.S. Pat. No. 6,534,091 discloses several types of products that contain a microcapsule formed with chitosan. However, no clear antiperspirant gel products containing visible capsules are known. This may be due to the problems associated with preparing compositions that maintain the desired clarity, while avoiding undesirable aesthetic attributes such as gritty feel and flaky film residues.

SUMMARY

The invention features clear personal care products containing visible capsules.

In one aspect the invention features a clear personal care composition, preferably an antiperspirant or deodorant composition, for topical application to the skin wherein the composition contains a plurality of visible capsules. By "visible" is meant visible to the naked eye (i.e., without magnification). The composition is preferably in the form of a clear gel that includes a solubilized antiperspirant salt.

In some implementations, the capsules enhance the aesthetic properties of the product, particularly by making the product visually interesting to the consumer, thereby prompting the consumer to purchase and use the product. The capsules may also be used to deliver an ingredient to a user's skin, thereby allowing ingredients to be included in the product that, if not encapsulated, would react with, inhibit or inactivate other ingredients in the composition, and/or that would affect the aesthetic properties of the product.

Preferably, the personal care composition is in the form of a gel, typically a gel that ranges from a cream to a soft solid to a solid stick. The composition preferably also includes a perspiration reducing effective amount of an antiperspirant salt and/or a malodor reducing effective amount of a deodorant active. Preferably, the capsules are uniformly dispersed throughout the composition.

The invention also features reducing perspiration from human skin by applying a perspiration reducing effective amount of the antiperspirant composition to the skin.

In another aspect, the invention features a personal care composition that includes a plurality of at least partially hydrated capsules dispersed within an emulsion.

The invention also features methods of making such compositions.

The invention also features a method of delivering an ingredient to the skin of a user of a personal care product, such as an antiperspirant gel or stick, by providing the ingredient in the personal care product in capsules, and selecting the hardness of the capsules so that the capsules will rupture when the product is applied to the skin.

The invention also features a method of increasing the amount of fragrance (including odor masking agents) in a clear gel composition, wherein the composition is an emulsion of a water phase and an oil phase, without deleteriously affecting the clarity of the composition. The method includes adding the fragrance to the oil phase (in which the fragrance is soluble) prior to formation of the emulsion and adjusting the refractive index of the water phase to within about 0.001 or less of the refractive index of the oil phase containing the fragrance, then combining the two phases to form the emulsion.

The capsules may be provided to enhance the aesthetic properties of the product. In addition, or instead, the capsules may be provided to deliver an ingredient to the user during use of the composition.

The capsules may be, for example, capsules that break during application of the product to the skin and are suitable for use with solid or water-insoluble ingredients, e.g., cellulosic capsules, or capsules that smear during application to the skin and are suitable for use with oil-soluble ingredients, e.g., wax-based capsules such as polyethylene-wax blends. If desired, both types of capsules may be used in a single composition.

In some implementations, the hardness of the capsules is selected to provide good user comfort during application of the product, while also allowing the capsules to be incorporated into the composition without damage to the capsules. The invention also features a method of manufacturing in which the capsules are hydrated to obtain a desired hardness. In some implementations, the capsules are prehydrated to a first hardness prior to incorporation into the composition, and the composition is formulated to allow the capsules to hydrate further, to a second, lower hardness, during a time period between manufacture and the expected initial use of the formulation by a consumer. In some implementations, pre-hydration is performed using a solution of an antiperspirant salt in water, or a liquid having the same composition as the water phase of the composition.

The personal care composition may include one or more of the following ingredients: water, an antiperspirant salt, a lower alkanol, a silicone oil, a surfactant, a volatile linear silicone, fragrances and deodorant actives.

The term "clear", as used herein, means that (1) the composition (without the capsules) has a sufficient clarity to allow Font 8 text to be read through a 1 cm thick layer of the composition at normal light; or (2) the composition (without the capsules) has a clarity better than 150 NTU (Nephelometric Turbidity Units) at 21° C. measured with an Orbeco-Hellige #965 Direct-Reading Turbidimeter. Preferred compositions have a sufficient clarity to allow the Font 8 text to be read through a 2 cm thick layer of the composition, or a clarity better than 100 NTU at 21° C.

In one embodiment, the composition may be in the form of an emulsion, either a water-in-oil emulsion or an oil-in-water emulsion, preferably a water-in-oil emulsion. Such an emulsion will preferably be in the form of a gel. Such a gel will typically have a viscosity of about 30,000 cP (30 Pas) to about 300,000 cP (300 Pas), preferably about 50,000 cP (50 Pas) to about 200,000 cP (200 Pas). The latter viscosity range is measured at 21° C. using a Brookfield RV viscometer with a helipath stand and T-C spindle at 5 RPM. Lower viscosities (30–50 Pas) can be measured with a T-B spindle at 5 RPM, and higher viscosities (200–300 Pas) can be measured with a T-D spindle at 5 RPM. The viscosity of the gel may be increased or decreased by changing the proportion of oil to water and/or by subjecting the composition to more or less high shear mixing. The composition may be made clear by either closely matching (e.g., to about 0.0005 or better) the refractive index of the two phases (see, for example, U.S. Pat. No. 5,587,153) or by formulating the product as a microemulsion (see, for example, WO 02/26204).

A microemulsion, as used herein, is a thermodynamically stable isotropic dispersion of oil and water containing domains of nanometer dimensions stabilized by an interfacial film of surface active agent(s). Microemulsions are clear because one or more dimensions of the domains is smaller than the wavelength of visible light (approximately 550 nanometers). The microemulsion may be, for example, an oil-in-water (o/w) microemulsion with discrete oil-swollen micelles or oil droplets; a water-in-oil (w/o) microemulsion with discrete water-swollen reversed micelles or water droplets; or a bicontinuous microemulsion. The bicontinuous microemulsion may be, for example, a sponge phase or "monolayer" bicontinuous microemulsion with two nearly equal volume immiscible fluids interlayered by a surfactant monolayer; a normal bicontinuous microemulsion including a water-rich bicontinuous phase with two immiscible fluids interlayered by a "normal" random-oriented lamellar-like surfactant double layers; or a reverse bicontinuous microemulsion including an oil-rich bicontinuous phase with two fluids immiscible interlayered by a "reversed" random-oriented lamellar-like surfactant double layers.

Preferred microemulsions form spontaneously and have good stability. The microemulsions are stable preferably for at least a day, more preferably at least 30 days, and most preferably at least 90 days, at room temperature. Stable, as used herein, means that the compositions retain clarity and that there is no visible phase separation within the compositions.

A further embodiment includes a gel composition formed by thickening or solidifying a carrier vehicle (e.g., a polyhydric alcohol such as propylene glycol) with a gellant (e.g. dibenzylidene sorbitol). Preferably, the vehicle and gellant are selected from those combinations that will form a clear gel composition. For those embodiments where the carrier vehicle includes a hydrophobic oil (e.g., a silicone oil), it will be advantageous to approximately match the average refractive index of the gellant to the average refractive index of the carrier vehicle.

Other features and advantages of the invention will be apparent from the description and drawings, and from the claims.

DETAILED DESCRIPTION

Figure 1:
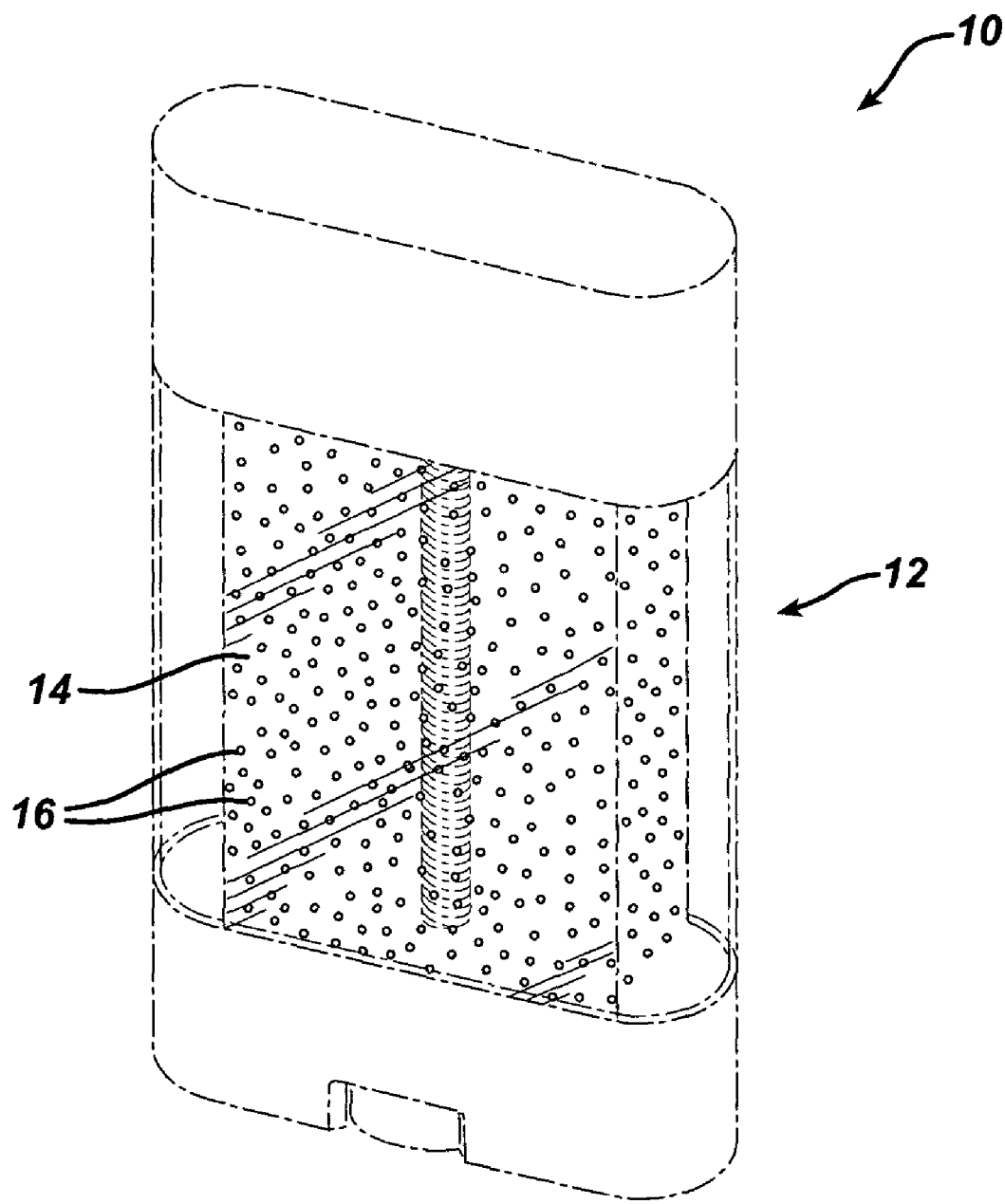
FIG. 1 is a perspective view of a clear gel antiperspirant product.

Referring to FIG. 1, a clear gel personal care product 10 includes a housing 12 containing a clear gel antiperspirant or deodorant composition 14 and, dispersed within the composition 14, a plurality of capsules 16. Preferably the capsules are visible to the naked eye (i.e., without magnification) and are included, at least in part, for aesthetic appeal. In addition, the capsules preferably are colored.

The composition and preparation of the capsules 16 will be discussed first, followed by a discussion of preferred gel compositions.

Capsules

Generally, suitable capsules will be of a composition that will not degrade during storage of the antiperspirant composition, and will not deleteriously affect the clarity of the composition. Because antiperspirants generally have a low pH, e.g., 3 to 4.5, it is generally necessary that the capsules be capable of withstanding a low pH environment without significant degradation, i.e., degradation that would deleteriously affect the clarity or other properties of the composition or cause the capsules to dissolve or rupture prematurely. Suitable capsules will also have a hardness that permits the composition to be manufactured and is suited to the application in which the composition will be used, as will be discussed below.

In a first embodiment, capsules 16 are cellulosic capsules, i.e., capsules containing cellulose as one component. Such capsules can also include other components, for example lactose, fructose, xylitol, glycerine, emulsifiers, sorbitol, dextrins and maltodextrins. Generally, the capsules include microcrystalline cellulose or hydroxypropyl methylcellulose and lactose. Suitable capsules of this type are commercially available under the tradename COSMOSPHERES, from Pelletech, Ltd., Switzerland, and UNISPHERES, from Induchem AG, Switzerland. These capsules are sold as hard, free-flowing particles that are water-insoluble but water-swellable.

Cellulosic capsules may be used to encapsulate solid or water-insoluble ingredients, such as colored pigments, vitamins, enzymes, plant extracts and silicones.

In many cases cellulosic capsules are generally too hard, as supplied, for use in personal care products, i.e., users may perceive such capsules as "scratchy", and the capsules will generally not rupture during normal application. Thus, if a soft, breakable capsule is desired it is generally necessary to hydrate the capsules, as will be discussed in detail below.

In another embodiment, the capsules 16 are polymeric/wax capsules, e.g., polyethylene wax capsules. Suitable capsules may include polyethylene, petrolatum, and ethylhexyl palmitate. These capsules may be used to encapsulate oil-soluble ingredients. Polymeric/wax capsules are available, for example, from Floratech Americas, Arizona, under the tradenames METASPHERES and METASOMES. Generally, polymeric/wax capsules are relatively soft as supplied, and do not require hydration or other pre-treatment to adjust their hardness. If it is necessary to adjust the properties of the capsules for use in a particular application, this may be adjusted by changing the formulation of the capsules, e.g., by selecting a polymer and/or wax having a higher or lower melting point.

The capsules may be used without any encapsulated ingredient, for aesthetic purposes alone, or may encapsulate an ingredient which is delivered to the user when the product is applied. If desired, several types of capsules can be used in a single product, containing different active ingredients. If an ingredient is encapsulated for delivery to the user upon application, it is important that the capsules rupture upon application. If the capsules are empty, it is nonetheless preferred that they rupture so that the capsules are not visible on the user's skin after application. It is generally preferred that the capsules be capable of disintegrating upon application so that no visible residue appears on the user's skin and there is no staining of the user's clothing.

If it is desired to encapsulate one or more ingredients in the capsules, suitable ingredients include but are not limited to the following: methyl lactate, tocopherols, e.g., tocopherol acetate (Vit. E), Evening Primrose Oil, colored pigments, titanium dioxide, ascorbyl palmitate, fragrances, octylmethoxycinnamate, PARSOL 1789 additive, triclosan, ubiquinone, retinyl palmitate, CERAMID 3 additive, melanin, panthenyl triacetate, tea tree oil, mal odor maskers, algae extract, benzophenone, beta-carotene (Vit. A), capric/caprylic triglyceride, L-ascorbic acid (Vit. C), Mentha Piperita (Peppermint Oil), pyridoxine dipalmitate, purified extract of Visnaga Vera, salicylic acid, mica, and talc.

The ingredient may also be selected from the following: glide enhancers, e.g., boron nitride; exfoliants, e.g., abrasive particles, loofah, and nylon; wetness, greasiness and oiliness reducing ingredients, e.g., starches, water lock agents, polypore, microsponge, silicone elastomers and absorbents; anti-caking agents, e.g., calcium phosphate, silicas, aluminosilicates and emollients; and ingredients that provide a sensation of coolness, e.g., menthol, menthyl lactate, and sodium palmitoyl proline.

Other suitable ingredients include vitamins (e.g., Vitamin E, Vitamin A, Vitamin C), adhesion agents, fragrances, deodorant actives (e.g., ACH, Famesol and octoxyglycerine), aluminum salts, talcs, efficacy enhancing agents (e.g., calcium chloride, for antiperspirants), odor modifiers (e.g., sodium bicarbonate), anti-irritants (e.g., allantoin), detackifiers (e.g., silicones, emollient esters and oils), water or encapsulated water, and anti-stain agents (e.g., Vitamin E and tocopherols).

These are only examples and many others may be used, as will be apparent to those of skill in the art.

Generally, the ingredients are encapsulated in the capsules by the manufacturer of the capsules. The manufacturer will customize capsules with a desired encapsulated ingredient. The capsules can contain, for example, 0.1 to 50% by weight of the ingredient, based on the dry weight of the capsules.

The concentration of the capsules in the composition will depend on the desired aesthetic properties of a particular product, and the amount of an encapsulated ingredient to be delivered. In some implementations, the concentration of capsules may range from about 0.05% to about 3%, preferably about 0.1% to 1.0%, more preferably about 0.2% to about 0.5%, by weight based on the weight of dry capsules.

The capsules can have any desired particle size, provided they are large enough to be visible without magnification. They should not be too large so as to interfere with delivery or use of the product. The particle size will generally be in the range of about 0.1 to 5 mm, more typically from about 0.5 to 1.5 mm. If desired, capsules having different particle sizes may be used in a single product, e.g., for interesting aesthetic effects. Generally the capsules will be spherical in shape, although elongated or ovoid shapes may be used (in which case the particle size is measured at the widest dimension).

As mentioned above, the capsules may be colored. Suitable colored capsules will not transfer color to the surrounding composition during storage, and will not stain the user's skin (unless application of a color is desirable) or clothing during use. Generally, color is provided by including a pigment in the capsule. Suitable pigments generally will not react deleteriously with the composition or with the user's skin, unless this reaction is counteracted by another component of the capsule. For example, some pigments, e.g., pigments containing sulfosilicates, may react in a low pH antiperspirant system and create malodorous compounds; however, this reaction can generally be inhibited by including other components, such as Vitamin A or E, in the capsules, rendering such pigments suitable for use.

The concentration of the pigment is selected to give an appealing color while preventing staining and residue upon application. In some implementations, the pigment concentration is from about 0.1 to 3.0% by weight of the dry capsules, e.g., from about 0.2 to 0.5%.

If desired, color change pigments can be used to provide a signal to the user, e.g., of application coverage or product drying. For example, a color change pigment that changes from colored to colorless can be used in a concentration that will be visible to the user after the capsules rupture during application, provided the pigment changes to its colorless state after application, to prevent staining.

Preferred Hardness of Capsules

Suitable capsules will be capable of withstanding processing without rupturing, but will be sufficiently breakable so that they will rupture during application of the composition to the user's skin and subsequently disintegrate leaving little or no residue. It is also generally preferred that the capsules feel soft, or cannot be felt at all, rather than feeling hard or scratchy when they contact the user's skin. These characteristics generally correlate well with the hardness of the capsules, as measured by a texture analyzer, e.g., using a Texture Analyzer type TA-XT2 (Texture Technologies Corporation, Scarsdale, N.Y.) according to the test procedure described below. It is generally preferred that the hardness of the capsules, measured in this manner, be from about 1 to 30 grams force.

In some implementations, capsules having a softness that will be optimum for user comfort and delivery of the encapsulated ingredient will be too soft to be easily incorporated into the composition without rupture of the capsules. For example, in some applications a hardness of from about 1 to 15 grams provides good properties during application to a user, but a hardness of from about 10 to 30 grams force is desirable for ease of processing. In the case of hydratable capsules, e.g., the cellulosic capsules described above, the capsules can be pre-hydrated to a first hardness that is suitable for processing, and then allowed to hydrate further, to a second hardness that is suitable for application, during shipment and storage of the product. This pre-hydration and subsequent "ripening" of the capsules will be discussed in further detail below.

However, in some cases the hardness of the capsules may be the same for both processing and final use during product application. For example, polymeric/wax capsules having a hardness of from about 1 to 10 grams may generally be processed without rupturing and also provide good product attributes.

The test procedure for determining hardness of capsules using Texture Analyzer type TA-XT2 is described below:

Hardness Test Procedure

Sample preparation: Capsules are placed directly on an aluminum slab and under plunger selected for hardness testing. If capsules have been removed from a composition remove excess composition from the capsules, e.g., by scraping with a spatula. The capsules should be aligned directly underneath the plunger before test is run.

Settings: Set computer to Texture Analyzer settings, version 05.16, load cell 5.0, hit F4, get menu, select measure force on compression and click return to start.

| Parameters: | Pre-Test speed | 2.0 mm/s |
|---|---|---|
| | Test speed | 0.2 mm/s |
| | Post test speed | 2.0 mm/s |
| | Rupture test distance | 1.0 mm/s |
| | Distance | 1.0 mm/s |
| | Force | 200 g |
| | Time | 5.0 sec |
| | Count | 5 |

After settings and parameters are retrieved, press SAVE

Testing hardness: After settings have been saved the actual test takes place. The plunger comes down, and will start to compress and break the capsules. Results are displayed in a chart representing Force (g) in the Y axis and Time in seconds in the X axis; the force is also displayed on the screen as a single unit and collected in a spread sheet.

In case of the dry capsules the maximum force required to break the capsules will be represented by the largest pick in the curve/chart and usually takes place within 0.5 sec to 1.0 seconds. For pre-hydrated capsules, the maximum force takes place within the first 0.2–0.3 seconds and the maximum force is represented by the maximum pick in the curve/chart.

Readings of maximum and minimum force can be obtained by zooming in the time range of 0.5–1.0 seconds for dry capsules and within the range of 0.2–0.3 seconds for pre-hydrated capsules. The hardness of polymeric/wax capsules is generally determined within the range of 0.1–0.2 seconds using the same setting as for cellulosic capsules. The hardness reading within these time frames determines how hard or soft the capsules are. A set of five readings are taken for each sample and the average of the five reading is reported as the hardness of the sample tested.

Hydration of Capsules

As discussed above, in the case of cellulosic capsules it may be necessary to hydrate the capsules prior to use of the product by the user, to reduce the hardness of the capsules. In certain antiperspirant products there may be insufficient available water to sufficiently hydrate the microspheres in situ, in the product. Thus, some degree of pre-hydration is generally needed before cellulosic capsules are incorporated into the composition.

Pre-hydration of the cellulosic capsules may be carried out by simply contacting the capsules in water, e.g., by immersion or spraying.

However, it is generally preferred that the capsules be hydrated in a solution that will inhibit microbial growth on the capsules, and act as a stabilizer for the capsules. Suitable solutions include solutions of antiperspirant salts in water, and solutions that contain, in addition to these components, an alcohol and a glycol. One suitable solution, for example, includes water, an aluminum-zirconium chlorohydrate glycine solution, ethyl alcohol, and propylene glycol. Hydrating in a relatively high solids solution, e.g., 35–45% solids, will also tend to reduce loss of water soluble components, such as lactose, from the capsules during hydration.

Alternatively, to prevent microbial growth the capsules may be hydrated in water containing a water-soluble antimicrobial, e.g., benzalkonium chloride and/or chlorhexidine digluconate, or an antimicrobial may be incorporated into the capsules during manufacture.

Suitable times for pre-hydration will vary depending on the size and composition of the capsules, the hydrating liquid used, and other parameters. A suitable hydration time to obtain a desired degree of hydration can be determined, for example, by periodically removing a sample of microspheres and testing their hardness as described above. Suitable hydration times range from 1 hour or less to several days.

In some implementations, the amount of hydrating liquid with which the capsules are contacted is controlled. The amount of liquid required for a desired degree of pre-hydration can be determined, e.g., by hydrating capsules to the desired extent and measuring the resulting weight gain of the capsules when excess surface liquid has been removed from the capsules. In some implementations, this weight gain is about 20–30%. Subsequently, the degree of hydration can be readily controlled, without the need to carefully control hydration time, by contacting the capsules with only the predetermined amount of liquid that is required. One suitable method of applying a controlled amount of liquid to the capsules includes spraying the hydrating liquid onto the capsules while maintaining the capsules in free rotating movement so as to distribute the liquid evenly over the surface of the capsules, e.g., in a rotating pan such as those used in coating pharmaceutical and confectionary pellets, or a V-Blender such as a Patterson Kelly Blender/Mixer (PK V-Blender type) or other rotating mixer. The liquid may be sprayed gradually onto the capsules, adding the liquid slowly and at intervals, e.g., of 1–5 minutes, so that at each addition only the surface of the capsules gets wet, and the liquid is absorbed and the capsules are free-flowing at the end of each addition. After mixing in this manner until all of the liquid is absorbed and the capsules are free flowing and do not stick to the mixer or each other, the capsules are allowed to sit, e.g., 12 to 48 hours, before adding them to the composition, to allow the liquid to become distributed through the capsules and the capsules to swell. The hardness of the capsules can be tested, as described above, to determine whether sufficient hydration has occurred. If the capsules are not to be immediately used, they should generally be stored in sealed containers, to prevent moisture loss which could result in a change in the hardness of the capsules.

After the capsules are added to the product, over time they will hydrate further as a result of contact between the capsules and water droplets of the emulsified water phase in the product. The degree of further hydration over time can be determined based on stability testing, in which the capsules are periodically removed from the product and their hardness is tested. Then, a nominal time period from manufacture to use can be assumed, and based on the stability testing and that assumption, the degree of pre-hydration can be adjusted so as to obtain a desired final level of hydration at the time of use.

Gel Compositions

The antiperspirant and deodorant gel compositions in which the capsules are dispersed are preferably water-in-oil emulsions in which the water phase comprises about 65% to 90% of the composition. The water phase is primarily water and has an antiperspirant salt or deodorant active dissolved therein in an amount to achieve an antiperspirant or deodorant effect. The water phase may also include lower alkanols, such as ethanol, and/or polyhydric alcohols (typically of 3 to 6 carbon atoms), such as propylene glycol, dipropylene glycol or sorbitol. If included in the composition, the total amount of lower alkanol will generally comprise less than 15% of the composition, preferably 10% or less, by weight. The amount of polyhydric alcohol will fall within the range of about 4 to 35% of the composition by weight. The polyhydric alcohol may be advantageously utilized to adjust the refractive index of the water phase so that it matches the refractive index of the oil phase (preferably to within about 0.0005) in order to achieve maximum clarity of the final composition. The gel composition should have a clarity better than 150 NTU (Nephelometric Turbidity Units), preferably better than 100 NTU, and most preferably better than 75 NTU at 21° C.

Antiperspirant salts which may be used in the compositions of the present invention include any of the conventional aluminum, zirconium and aluminum-zirconium salts known to be useful in antiperspirant compositions. These salts include aluminum halides and aluminum hydroxy halides (e.g. aluminum chlorohydrate), and mixtures or complexes thereof with zirconyl oxyhalides and zirconyl hydroxyhalides (e.g. aluminum-zirconium chlorohydrate). The antiperspirant salts are utilized in solubilized form—i.e. they are dissolved in water, alcohol, polyhydric alcohol, aqueous alcohol, or aqueous polyhydric alcohol—when formulated into the gel compositions of the present invention. Preferably, the antiperspirant salts are utilized as aqueous solutions, typically of about 30 to 50% concentration. Most preferably, such solutions are not prepared by redissolving spray dried salts since spray dried salts have oxides which can cause cloudiness in the final composition.

Preferred aluminum salts are those having the general formula $Al_2(OH)_{6-a}X_a$ wherein X is Cl, Br, I or $NO_3$, and a is about 0.3 to about 5, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_5$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 2 to about 10, and a metal:X+Y ratio of about 0.9 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to about 1:5.

It may be desirable to utilize enhanced efficacy aluminum and aluminum-zirconium antiperspirant salts in the compositions of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0,7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers. An especially preferred enhanced efficacy antiperspirant salt is one which includes a water soluble calcium salt as described in U.S. Pat. No. 6,245,325, which is incorporated herein by reference.

Sufficient antiperspirant salt should be added so that the final composition, after all components are added, includes between about 3% and about 30%, preferably about 6% to about 25%, of the antiperspirant salt by weight. Generally, the composition will be designated an antiperspirant composition if it contains sufficient antiperspirant salt to effectively inhibit perspiration. This amount of antiperspirant salt will typically be greater than about 10% by weight. Below that amount, the composition will generally be designated a deodorant composition. It should be noted that reference throughout this application to weight percent of antiperspirant salt is intended to be calculated in accordance with the standard industry method, which includes bound water and glycine. If the amount of antiperspirant salt is calculated in accordance with the U.S.P. method, which excludes bound water and glycine, the range of suitable weight percents for inclusion in the composition will be somewhat lower than that stated above.

The oil phase comprises about 10% to 35% of the composition. Generally the oil phase comprises a silicone oil and/or other organic oil. The oil phase is the continuous phase and provides emolliency while reducing the wetness of the composition. The oil phase also includes a surfactant material which is effective in emulsifying the water phase into the oil phase. A preferred surfactant material is a polyether substituted silicone such as dimethicone copolyol. A suitable surfactant is DC 5225C (Dow Coming), which is a blend of cyclomethicone (D5) and dimethicone copolyol (PEG/PPG-18/18 Dimethicone).

The gel composition also preferably includes a volatile linear silicone. This volatile linear silicone is a polydimethylsiloxane or dimethicone which has a relatively low average molecular weight, a relatively low viscosity and a significant vapor pressure at 25° C. (i.e. one gram of fluid placed on No. 1 filter paper leaves substantially no visible residue after thirty minutes at room temperature). It also typically has a boiling point under 250° C. The volatile linear silicone (or volatile dimethicone) is represented by the formula $(CH_3)_3SiO(Si(CH_3)_2O)_nSi(CH_3)_3$ in which n is an integer of about 0 to about 6, preferably about 1 to about 4. One of the methyl groups of the foregoing formula may be replaced with an alkyl group (e.g. of 2 to 10 carbon atoms) to provide an alkylmethylsiloxane. Such material includes, for example, DC 2-1731 (Dow Coming), which is 3-hexylheptamethyltrisiloxane (viscosity=1.0 cst).

While a pure silicone polymer may be utilized, generally the volatile linear silicone is a mixture of silicone polymers of the above formula. The volatile linear silicone will have a viscosity of less than about 5 cst (or less than about 5 cP), preferably between about 0.6 and 3.0 cst, more preferably between 1.0 and 2.0 cst. (For silicones with a specific gravity at 25° C. in the 0.75 to 0.92 range, the foregoing viscosity ranges convert to about 0.5 to 2.8 cP, preferably about 0.8 to 1.8 cP) Suitable volatile linear silicones include DM Fluid 0.65 cs (hexamethyldisiloxane), DM Fluid 1.0 cs (octamethyltrisiloxane), DM Fluid 1.5 cs, DM Fluid 2.0 cs (dodecamethylpentasiloxane), DC 2-1184 and DC 2-1731, all available from Dow Coming. DC 2-1184, which has a viscosity of about 1.7 cst and an average molecular weight of about 320 (i.e. n is about 1 to 3 in the above formula), is preferred.

The amount of volatile linear silicone to be incorporated into the composition may be varied depending on the nature of the particular volatile linear silicone utilized and the other oil components present in the composition. That is, one may balance the amount of volatile linear silicone and the amount of non-volatile oil in order to achieve the desired balance of non-staining versus non-stickiness or emolliency. Generally, the volatile linear silicone will be utilized in an amount of about 2 to 15%, preferably about 3 to 10% of the composition by weight.

The oil phase may also comprise a sufficient amount of a non-volatile emollient oil in order to provide the final composition with desirable application aesthetics, particularly emolliency and non-stickiness. Suitable non-volatile silicones, include dimethicone (e.g. DC 225, available from Dow Coming) and a combination of dimethicone and DC 2–1184 silicone. The composition may also contain a non-volatile organic oil (or a mixture of organic oils), which may be used alone or in combination with a non-volatile silicone. Generally, the final composition will comprise less than about 5% by weight of non-volatile oil. Preferably, the composition will comprise from 0 to 5%, most preferably about 1 to 4%, of non-volatile silicone by weight. In formulations containing low amounts of antiperspirant salt (i.e. about 10% or less), it may be possible and desirable to remove all of the non-volatile oil. In such a case, the silicone oil component may include only the volatile linear silicone and optionally a volatile cyclic silicone.

As mentioned previously, the oil phase also includes a surfactant material, the type and amount of which is selected to emulsify the water phase within the oil phase. Preferably, the surfactant material is a polyether substituted silicone such as dimethicone copolyol. Generally, the composition will comprise about 0.5 to 1.5% of dimethicone copolyol (PEG/PPG-18/18 Dimethicone). Advantageously, the dimethicone copolyol may be added as a blend with cyclomethicone. A typical blend is DC 5225C (Dow Coming), which contains about 90% cyclomethicone (cyclopentasiloxane, DC 245) by weight. If added as such a blend, then the cyclomethicone and dimethicone copolyol blend will comprise about 5 to 15%, preferably about 7 to 10%, of the composition by weight. The cyclomethicone also contributes to the overall application aesthetics of the product, such as dryness. Naturally, of course, a volatile cyclic silicone may be included in the composition of the present invention as a separate component, if desired. If separately added, the volatile cyclic silicone will generally comprise about 0 to 18%, preferably about 5 to 15%, of the composition by weight.

The antiperspirant composition may include other conventional ingredients. These include, for example, gelling agents, fragrances, emollients, bactericides, paraffinic hydrocarbons such as mineral oil and hydrogenated polyisobutene, fatty alcohol esters such as C12–C15 alcohols benzoate and myristyl octanoate, fatty acid esters such as isopropyl palmitate, myristyl myristate and octyl isononanoate, dicarboxylic acid esters such as diisopropyl sebacate, fatty amides such as Stearamide MEA and Lauramide DEA, polyethylene glycols and polypropylene glycols such as PEG-40 and PPG-20, polyethylene and/or polypropylene glycol ethers of C4–20 alcohols such as PPG-10 butanediol, PPG-5-Buteth-7, PPG-3-Myreth-3, and Steareth-20, and polyethylene and/or polypropylene glycol esters of C4–20 acids such as PEG-8 Distearate and PEG-10 Dioleate.

The foregoing list of materials is by way of example only and is not intended to be a comprehensive list of all potential materials that may be useful in an antiperspirant composition. Obviously, the skilled worker may select those materials which provide the desired application and aesthetic characteristics of the particular form of antiperspirant composition to be produced.

Perspiration is reduced or inhibited by topically applying an effective amount of an antiperspirant composition to the skin of a human, preferably to the axilla, where such reduction in perspiration is desired by the user. An effective amount is that amount which provides at least a 20% sweat reduction, preferably at least a 40% sweat reduction, when tested in accordance which has a standard hot room thermal efficacy protocol, and most preferably that amount which reduces perspiration to a degree that is noticeable by the user. Typically, the amount of antiperspirant composition applied will range from about 0.1 grams to about 1.0 grams per axilla depending on the formulation or such amount as will deliver about 0.01 to about 0.25 grams of antiperspirant active per axilla.

In some cases, it is desirable to include an ingredient in the composition that has a refractive index that is higher than that of the emulsion, i.e., a relatively high refractive index (e.g., nD@21° C. of greater than of 1.5, typically on the order of nD@21° C. of 1.5160–1.5165). For example, certain fragrances have a relatively high refractive index. We have found that such ingredients can be added to the composition in relatively high concentrations, without compromising clarity, by adding the ingredient(s) to the phase in which it is soluble, e.g., the oil phase for an oily, water-insoluble ingredient, and then adjusting the refractive index of the other phase, e.g., the water phase in the above example, to compensate for the change in refractive index caused by the addition. The refractive index of the other phase can be adjusted, for example, by increasing the solids level of that phase. For example, in the compositions described above, the polyhydric alcohol (e.g., propylene glycol) can be increased in the water phase until the matching refractive index is obtained, with a proportional recalculation of the other ingredients in the water phase to adjust the formula for a total of 100%. Using this technique, in combination with providing some of the same ingredient in the capsules, it is possible to include levels of certain ingredients that normally would be difficult or impossible to add to a clear gel product while maintaining its clarity and other desirable attributes. For example, it is possible to add an amount of fragrance that is sufficient to significantly increase the time before malodor breakthrough during use of the antiperspirant.

Addition of Capsules to the Composition

Because antiperspirant gels are generally prepared under high shear conditions that would destroy the capsules, if the composition is a gel the capsules are added after the gel has been formed. The capsules may be added directly to the gel in their final concentration, e.g., using a Ross Mixer, or may be mixed with a smaller amount of gel to form a concentrate which is then added in an appropriate amount to the gel to form the final product. Generally, the capsules are added at a suitable stage in the process, and under sufficiently low shear, so that the capsules will not rupture during mixing. The capsules may be incorporated by first mixing them with a relatively small quantity of the composition to form a concentrate, and then adding the concentrate to the composition in a desired final proportion. The capsules may also be added as an in-line step in a continuous manufacturing process.

These methods are suitable for both cellulosic and polymeric/wax capsules.

The present invention may be further illustrated by the following examples in which the parts and percentages are by weight.

EXAMPLE

A clear antiperspirant gel composition comprising the following ingredients, in which all parts and percentages are by weight, was prepared in the following manner. The water phase components (antiperspirant salt, propylene glycol, ethanol, water) and the oil phase components are each mixed in separate containers and filtered and the refractive index of each is measured. The refractive index of the water phase is adjusted to match the refractive index of the oil phase to within 0.0004 by addition of water or propylene glycol as required. The water phase is then slowly added to the oil phase at about 18° C. with sufficient mixing to form a clear emulsion with minimum aeration. This emulsion is then sheared to form a clear gel with a viscosity of about 130,000 to 160,000 cP (130–160 Pas). The capsules are blended with a small amount of the clear gel composition to form a concentrate, which is then blended with the remainder of the clear gel composition.

| Ingredient | Weight Percent |
| --- | --- |
| Water (and) Aluminum Zirconium Tetrachloro-hydrex Gly (29.0%) (and) CaCl$_2$ (1.63%)[1] | 60.19 |
| Water | 7.57 |
| Ethanol | 10.92 |
| Propylene Glycol | 2.98 |
| Cyclopentasiloxane (and) PEG/PPG-18/18 Dimethicone[2] | 9.52 |
| Dimethicone[3] | 1.74 |
| Dimethicone & Trisiloxane[4] | 6.09 |
| Colored capsules[5] | 0.35 |
| Fragrance | 0.64 |

[1] Aqueous antiperspirant salt contains about 1.8% Ca and about 3.4% Glycine
[2] DC-5225C (Dow Corning)
[3] DC 200 (10 cst) (Dow Corning)
[4] DC 2-1184 (1.7 cst) (Dow Corning)
[5] Unispheres BHCG-601 (Induchem AG) - Lactose (and) Cellulose (and) Hydroxypropyl Methyl Cellulose (and) fragrance (1%) (and) pigment (0.5%)

While particular embodiments of the invention have been shown and described for illustrative purposes, it will be apparent to those skilled in the art that various changes and modifications may be made without departing from the spirit and scope of the invention, which is defined by the claims that follow.

For example, while clear gel emulsion compositions are described above, the capsules described herein may be used in other types of compositions, e.g., compositions in the form of clear solid sticks, clear soft solids and clear creams If the product is a deodorant product that does not contain an antiperspirant salt, it may not be necessary for the capsules to be able to withstand a low pH environment. Moreover, while many cellulosic capsules require the pre-hydration described above, some cellulosic capsules may be obtained in a pre-ripened state. Suitable pre-ripened capsules include, for example, those sold by Hallcrest, Ltd., Poole, England, under the product designation D/HC 940.

What is claimed is:

1. An antiperspirant or deodorant composition for topical application to the skin, said composition being in the form of a clear gel comprising a solubilized antiperspirant salt and having a plurality of visible capsules dispersed therein.

2. The composition of claim 1 wherein the clear gel is in the form of a cream, soft solid or solid stick.

3. The composition of claim 2 wherein the clear gel comprises an emulsion, a microemulsion or a vehicle thickened or solidified with a gelling agent.

4. The composition of claim 3 wherein the clear gel comprises a water-in-oil emulsion.

5. The composition of claim 1 or 4 wherein the capsules have a hardness of from about 1 to 30 grams force.

6. The composition of claim 5 wherein the capsules are at least partially hydrated.

7. The composition of claim 6 wherein the capsules are substantially completely hydrated, and have a hardness of from about 1 to 15 grams force.

8. The composition of claim 7 wherein the capsules, prior to addition to the composition, have a hardness of from about 10 to 30 grams force.

9. The composition of claim 1 or 4 wherein the capsules comprise cellulosic capsules.

10. The composition of claim 1 or 4 wherein the capsules comprise polymeric/wax capsules.

11. The composition of claim 1 or 4 wherein the capsules comprise a colorant.

12. The composition of claim 1 or 4 wherein the capsules include an ingredient for application to the skin, and wherein the capsules are adapted to rupture when the composition is applied to the skin, thereby releasing the ingredient.

13. The composition of claim 1 or 4 wherein the capsules have a particle size of about 0.1 to 5 mm.

14. The composition of claim 1 or 4 wherein the capsules have a particle size of about 0.5 to 1.5 mm.

15. A method of manufacturing a personal care composition containing visible capsules, comprising:
    (a) providing hydratable capsules;
    (b) thereafter pre-hydrating the hydratable capsules; and
    (c) incorporating the pre-hydrated capsules into a personal care composition.

16. The method of claim 15 further comprising, between step (a) and step (b), measuring the hardness of the capsules.

17. The method of claim 15 wherein the capsules comprise cellulosic capsules.

18. The method of claim 15 wherein the pre-hydrating step comprises contacting the capsules with an aqueous solution containing an antiperspirant salt.

19. The method of claim 18 wherein the solution further comprises an alcohol and a glycol.

20. The method of claim 15 wherein the pre-hydrating step comprises spraying liquid onto the capsules.

21. The method of claim 15 wherein the capsules are incorporated by first mixing them with a portion of the composition to form a concentrate, and then adding the concentrate to the remainder of the composition in a desired final proportion.

22. An antiperspirant or deodorant composition for topical application to the skin, said composition being in the form of a clear gel comprising a solubilized antiperspirant salt and having a plurality of visible capsules dispersed therein,
    wherein the plurality of visible capsules are included in the composition at a concentration level of from about 0.05% to about 3%, by weight based on the weight of the capsules.

23. An antiperspirant or deodorant composition for topical application to the skin, said composition being in the form of a clear gel comprising a solubilized antiperspirant salt and having a plurality of visible capsules dispersed therein,
    wherein the capsules have a paticle size of 0.5 to 1.5 mm.

* * * * *